US010251574B2

(12) United States Patent
Hayashi et al.

(10) Patent No.: US 10,251,574 B2
(45) Date of Patent: Apr. 9, 2019

(54) BIOLOGICAL INFORMATION MEASUREMENT DEVICE

(71) Applicant: Murata Manufacturing Co., Ltd., Nagaokakyo-shi, Kyoto-fu (JP)

(72) Inventors: Takanori Hayashi, Nagaokakyo (JP); Yasushi Sato, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 197 days.

(21) Appl. No.: 15/133,390

(22) Filed: Apr. 20, 2016

(65) Prior Publication Data
US 2016/0228022 A1    Aug. 11, 2016

Related U.S. Application Data

(63) Continuation of application No. PCT/JP2014/076761, filed on Oct. 7, 2014.

(30) Foreign Application Priority Data

Oct. 31, 2013   (JP) ................................. 2013-227731

(51) Int. Cl.
*A61B 5/00*     (2006.01)
*A61B 5/04*     (2006.01)
(Continued)

(52) U.S. Cl.
CPC ........ *A61B 5/04014* (2013.01); *A61B 5/0245* (2013.01); *A61B 5/02416* (2013.01);
(Continued)

(58) Field of Classification Search
CPC .................. A61B 5/04014; A61B 5/02416
(Continued)

(56) References Cited

U.S. PATENT DOCUMENTS 8,597,196 B2    12/2013   Kishi et al.
8,643,362 B2     2/2014   Sekiguchi et al.
(Continued)

FOREIGN PATENT DOCUMENTS

JP    H10285021 A    10/1998
JP    2003028952 A    1/2003
(Continued)

OTHER PUBLICATIONS

International Search Report issued for PCT/JP2014/076761, dated Dec. 9, 2014.
(Continued)

*Primary Examiner* — Nadia A Mahmood
(74) *Attorney, Agent, or Firm* — Arent Fox LLP

(57) ABSTRACT

A biological information measurement device includes a photoplethysmographic sensor that detects a photoplethysmographic signal, an envelope detection processor that generates an envelope of the photoplethysmographic signal, and an amplitude normalization processor that normalizes amplitude of the photoplethysmographic signal to a desired amplitude value based on amplitude of the envelope. The device further includes an adaptive line spectrum enhancer that is capable of varying a filter coefficient, suppressing an aperiodic component contained in the normalized photoplethysmographic signal, and outputting a periodic component. A biological information obtainment unit is provided to obtain biological information such as a pulse rate based on an output signal from the adaptive line spectrum enhancer.

20 Claims, 10 Drawing Sheets

(51) Int. Cl.
*A61B 5/0408* (2006.01)
*A61B 5/024* (2006.01)
*A61B 5/0245* (2006.01)

(52) U.S. Cl.
CPC ........ *A61B 5/0408* (2013.01); *A61B 5/04017* (2013.01); *A61B 5/725* (2013.01); *A61B 5/7207* (2013.01)

(58) Field of Classification Search
USPC .......................................................... 600/519
See application file for complete search history.

(56) References Cited

U.S. PATENT DOCUMENTS

| 2011/0227571 A1 | 9/2011 | Sekiguchi et al. |
| 2013/0197377 A1* | 8/2013 | Kishi .................... A61B 5/721 600/508 |

FOREIGN PATENT DOCUMENTS

| JP | 2011189079 A | 9/2011 |
| JP | 2012024320 A | 2/2012 |
| JP | 2012165915 A | 9/2012 |
| JP | 2013063208 A | 4/2013 |
| JP | 2013153782 A | 8/2013 |

OTHER PUBLICATIONS

Written Opinion of the International Searching Authority issued for PCT/JP2014/076761, dated Dec. 9, 2014.

* cited by examiner

BIOLOGICAL INFORMATION MEASUREMENT DEVICE

CROSS REFERENCE TO RELATED APPLICATIONS

The present application is a continuation of PCT/JP2014/076761 filed Oct. 7, 2014, which claims priority to Japanese Patent Application No. 2013-227731, filed Oct. 31, 2013, the entire contents of each of which are incorporated herein by reference

FIELD OF THE INVENTION

The present invention relates to a biological information measurement device.

BACKGROUND

Biological signals such as electrocardiographic waves and photoplethysmographic waves have characteristics that artifacts (noise) due to body motion or the like is easy to be superimposed thereon. Patent Document 1 discloses a biological signal measurement device that extracts and detects a pulsation component of a subject from a measured signal superimposed with noise components such as an artifact component.

The biological signal measurement device includes a light irradiator that irradiates a biological tissue of the subject with two light components having different wavelengths, a light receiver that receives the light components having the respective wavelengths, which have been emitted from the light irradiator and have transmitted through or have been reflected by the biological tissue, and converts the light components to electric signals (biological signals) in accordance with light reception intensities of the respective light components, a Hilbert transformation unit that performs Hilbert transformation on the electric signals so as to generate pieces of envelope data forming envelopes, and an oxygen saturation calculator that calculates an extinction ratio based on the generated pieces of envelope data and calculates blood oxygen saturation in the artery in the biological tissue based on the extinction ratio.

Further, the biological signal measurement device measures the blood oxygen saturation by detecting the envelopes of the electric signals (biological signals) by the Hilbert transformation unit and performing normalization processing on amplitudes thereof. In addition, the biological signal measurement device relatively attenuates components other than a frequency component (pulsation component) in accordance with pulsation of the artery of the subject so as to calculate a pulse rate.

Patent Document 1: Japanese Unexamined Patent Application Publication No. 2012-024320.

The biological signal measurement device as disclosed in Patent Document 1 can deal with unexpected artifacts. However, the biological signal measurement device cannot sufficiently remove artifacts for a biological signal with the artifacts superimposed thereon steadily, resulting in a risk that the pulse rate cannot be calculated accurately. Therefore, a technique capable of removing artifacts more effectively and obtaining biological information robustly against the artifacts has been desired.

SUMMARY OF THE INVENTION

The present invention has been made in order to solve the above-described problem and an object thereof is to provide a biological information measurement device configured to effectively remove artifacts due to body motion or the like, which have been superimposed on a biological signal, and to obtain biological information robustly against the artifacts.

A biological information measurement device according to an aspect of the invention includes a biological signal detecting unit that detects a biological signal, an envelope detecting unit that generates an envelope of the biological signal, an amplitude normalizing unit that normalizes amplitude of the biological signal to a desired amplitude value based on amplitude of the envelope, an adaptive filter that is capable of varying a filter coefficient, suppresses an aperiodic component contained in the biological signal normalized by the amplitude normalizing unit, and allows passage of a periodic component, and a biological information obtainment unit that obtains biological information based on an output signal from the adaptive filter.

With the biological information measurement device according to the aspect of the invention, amplitude values of signals which are input to the adaptive filter can be made substantially constant because the amplitude normalizing unit that normalizes the amplitude of the biological signal to the desired amplitude value based on the amplitude of the envelope is provided at a previous stage of the adaptive filter. Therefore, a sum of input power in the adaptive filter is substantially constant and a step-size parameter as a necessary and sufficient condition for convergence of the adaptive filter can be set previously when a least mean square (LMS) method is used, for example. Further, an adverse effect on the convergence of the adaptive filter by variation in the amplitude of the biological signal due to individual difference can be also absorbed. Therefore, the adaptive filter can be made to adapt appropriately so as to extract a frequency component of the biological signal. Further, even when the artifacts are superimposed continuously, they can be removed by the adaptive filter. As a result, artifacts due to body motion or the like, which have been superimposed on the biological signal, can be removed effectively and biological information can be obtained robustly against the artifacts.

It is preferable that the biological information measurement device according to the aspect of the invention further include a filter coefficient updating unit which controls execution and stop of update of the filter coefficient of the adaptive filter based on the amplitude of the envelope.

According to the exemplary embodiment, execution and stop of the update of the filter coefficient of the adaptive filter are controlled based on the amplitude of the envelope. Therefore, inappropriate learning of the adaptive filter can be prevented by controlling (for example, stopping) the update of the filter coefficient appropriately when an excessively large or small biological signal is input.

In the biological information measurement device according to the aspect of the invention, it is preferable that the envelope detecting unit include a full-wave rectifying circuit which full-wave rectifies the biological signal, and a low-pass filter which allows selective passage of a low-frequency component contained in the biological signal full-wave rectified by the full-wave rectifying circuit and generates the envelope of the full-wave rectified biological signal. With this, the envelope of the biological signal can be extracted appropriately.

It is preferable that the biological information measurement device according to the aspect of the invention further include a basic frequency amplifying unit which makes peaks remain from an impulse biological signal detected by the biological signal detecting unit, monotonously decreases the signal between the peaks more moderately than the original biological signal, reduces a harmonic component of a basic frequency contained in the biological signal, amplifies a signal component of the basic frequency, and outputs the signal to the envelope detecting unit and the amplitude normalizing unit.

In this case, the basic frequency component of the biological signal is amplified. Therefore, even when a biological signal (for example, a biological signal with harmonic waves, such as an impulse sequence (for example, electrocardiographic waveform and ballistocardiographic waveform)) having characteristics that the adaptive filter is difficult to adapt for it is input, the adaptive filter can be made to adapt for the biological signal. Therefore, the biological information can be stably obtained from the biological signal superimposed with artifacts.

It is preferable that the biological information measurement device according to the aspect of the invention further include a low-pass filter which is interposed at a subsequent stage of the basic frequency amplifying unit, allows selective passage of the signal component of the basic frequency contained in the biological signal output from the basic frequency amplifying unit, and suppresses passage of the harmonic component of the basic frequency.

In this case, a spectrum of the basic frequency of the biological signal can be further enhanced by applying the low-pass filter to the biological signal.

According to the invention, artifacts due to body motion or the like, which have been superimposed on a biological signal, can be removed effectively and biological information can be obtained robustly against the artifacts.

DETAILED DESCRIPTION

Figure 1:
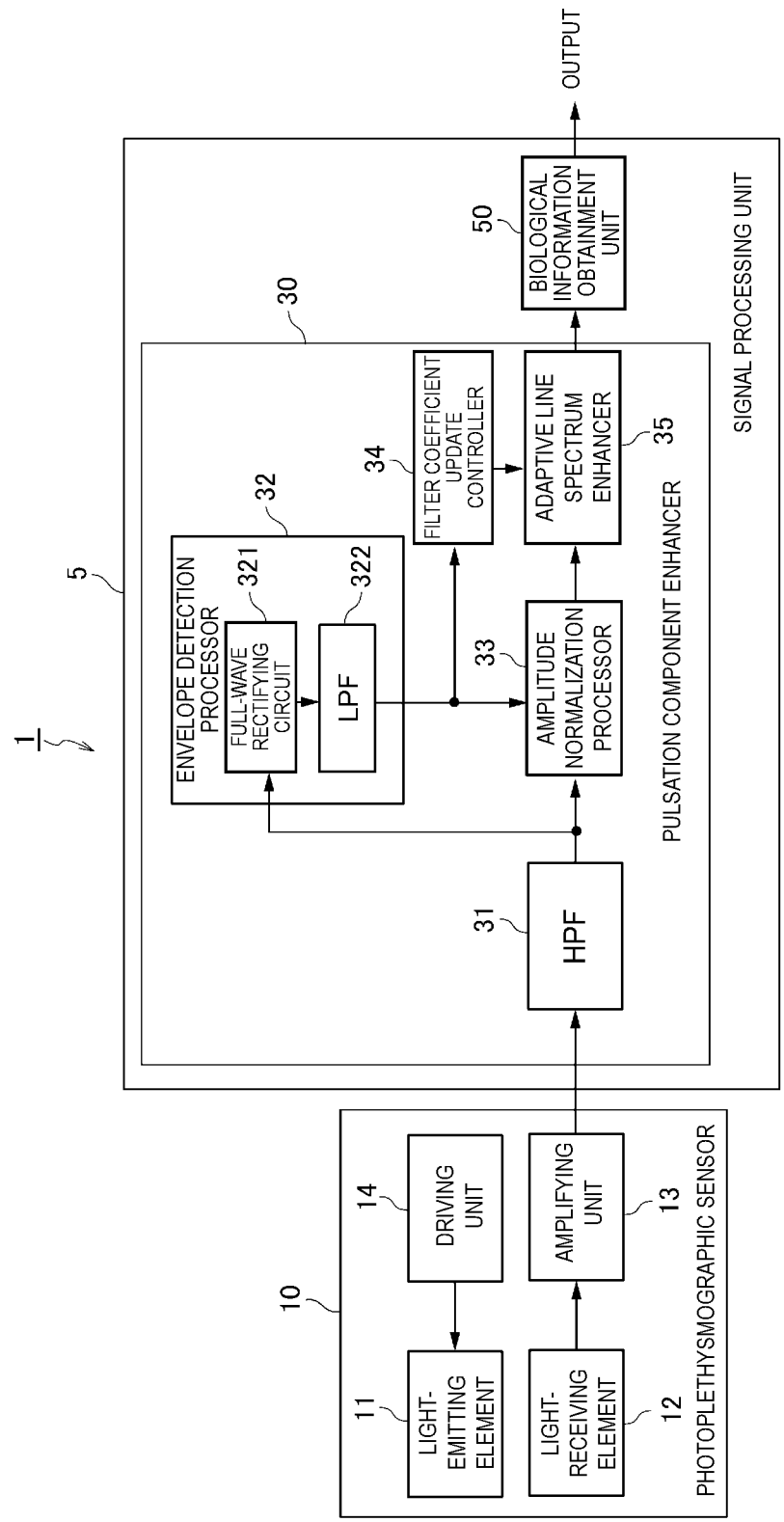
FIG. 1 is a block diagram illustrating the configuration of a biological information measurement device according to a first embodiment.

Hereinafter, preferred embodiments of the invention will be described in detail with reference to the drawings. It should be noted that the same reference numerals denote the same or equivalent portions in the drawings. In the individual drawings, the same reference numerals denote the same constituent components and overlapped description thereof is omitted.

First Embodiment

Figure 2:
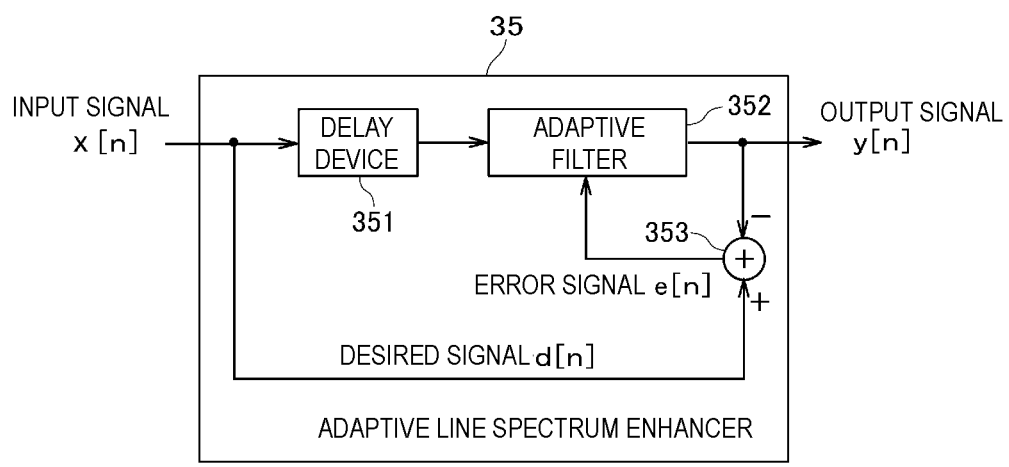
FIG. 2 is a block diagram illustrating the configuration of an adaptive line spectrum enhancer configuring the biological information measurement device in the first embodiment.

First, the configuration of a biological information measurement device 1 according to a first embodiment will be described with reference to FIG. 1 and FIG. 2 in combination. FIG. 1 is a block diagram illustrating the configuration of the biological information measurement device 1. FIG. 2 is a block diagram illustrating the configuration of an adaptive line spectrum enhancer 35 configuring the biological information measurement device 1. In the embodiment, the case in which biological information such as a pulse rate is measured from a photoplethysmographic signal as a biological signal. It is sufficient that the biological signal is a signal in which a spectrum of a pulsation component is dominant, such as the photoplethysmographic signal, and the biological signal is not limited to the photoplethysmographic signal.

The biological information measurement device 1 detects the photoplethysmographic signal, for example, removes an artifact signal generated due to body motion or the like, which has been superimposed on the photoplethysmographic signal, and measures biological information such as the pulse rate more robustly against artifacts. Therefore, the biological information measurement device 1 includes a photoplethysmographic sensor 10 that generates the photoplethysmographic signal and a signal processing unit 5 that removes the artifact signal superimposed on the photoplethysmographic signal and measures the biological information such as the pulse rate. Hereinafter, individual constituent components will be described in detail.

The photoplethysmographic sensor 10 is a sensor that optically detects the photoplethysmographic signal using light absorption characteristics of hemoglobin in blood. That is to say, the photoplethysmographic sensor 10 functions as a biological signal detecting unit in the scope of the disclosure herein. The photoplethysmographic sensor 10 is configured by including a light-emitting element 11, a light-receiving element 12, an amplifying unit 13, and a driving unit 14.

The light-emitting element 11 emits light in accordance with a pulsed driving signal that is generated and output by the driving unit 14. For example, a light emitting diode (LED), a vertical cavity surface emitting laser (VCSEL), a resonator-type LED, or the like can be used for the light-emitting element 11.

The light-receiving element 12 outputs a detection signal in accordance with intensity of light that has been emitted from the light-emitting element 11, has transmitted through a human body such as a finger tip or has been reflected by the human body, and has been incident thereon. For example, a photo diode, a photo transistor, or the like is preferably used for the light-receiving element 12. In the embodiment, the photo diode is used for the light-receiving element 12. The light-receiving element 12 is connected to the amplifying unit 13 and the detection signal (photoplethysmographic signal) obtained by the light-receiving element 12 is output to the amplifying unit 13.

The amplifying unit 13 is configured by an amplifier using an operational amplifier or the like, for example, and amplifies the photoplethysmographic signal detected by the light-receiving element 12. The photoplethysmographic sensor 10 is connected to the signal processing unit 5 and outputs the detected photoplethysmographic signal to the signal processing unit 5.

The signal processing unit 5 applies the adaptive line spectrum enhancer 35 as one type of an adaptive filter to the photoplethysmographic signal detected by the photoplethysmographic sensor 10 to remove an artifact signal generated due to body motion or the like, which has been superimposed on the photoplethysmographic signal, and measures the biological information such as the pulse rate (basic frequency of the biological signal). Therefore, the signal processing unit 5 includes a pulsation component enhancer 30 that removes an artifact component contained in the input photoplethysmographic signal and a biological information obtainment unit 50 that measures the biological information such as the pulse rate from the photoplethysmographic signal from which the artifacts have been removed. Further, the pulsation component enhancer 30 is configured by including a high-pass filter (HPF) 31, an envelope detection processor 32, an amplitude normalization processor 33, a filter coefficient update controller 34, and the adaptive line spectrum enhancer 35.

Among the above-described individual parts, the amplitude normalization processor 33, the filter coefficient update controller 34, the adaptive line spectrum enhancer 35, and the biological information obtainment unit 50 can be functional units or modules that are configured by a central processing unit (CPU) (or micro controller unit (MCU)) that performs arithmetic operation processing, a read only memory (ROM) that stores therein programs and pieces of data for causing the CPU to execute pieces of processing, a random access memory (RAM) that temporarily stores therein pieces of data of various types such as arithmetic operation results, and the like. That is to say, the CPU executes the programs stored in the ROM, so that the above-described individual functions are made to operate. The present disclosure refers to each specific unit performing its associated algorithm, but it should be appreciated that such algorithms can be performed by the CPU according to the exemplary embodiment.

The HPF 31 cuts a direct-current (DC) component of the input photoplethysmographic signal. It should be noted that the photoplethysmographic signal from which the DC component has been cut by the HPF 31 is output to each of the envelope detection processor 32 and the amplitude normalization processor 33.

According to an exemplary embodiment, the envelope detection processor 32 is comprised by circuitry that includes a full-wave rectifying circuit 321 that rectifies the photoplethysmographic signal and a low-pass filter (LPF) 322 that selectively passes a low-frequency component contained in the full-wave rectified photoplethysmographic signal and generates an envelope of the photoplethysmographic signal. That is to say, the envelope detection processor 32 functions as an envelope detecting unit in the scope of the disclosure herein. Thus, when the photoplethysmographic signal has a waveform close to a sine wave, an average amplitude value thereof is 2/π-fold of a maximum amplitude value. Therefore, the envelope of the photoplethysmographic signal is obtained by multiplying the signal which has been full-wave rectified and has been subject to the LPF 322 by π/2.

Figure 3:
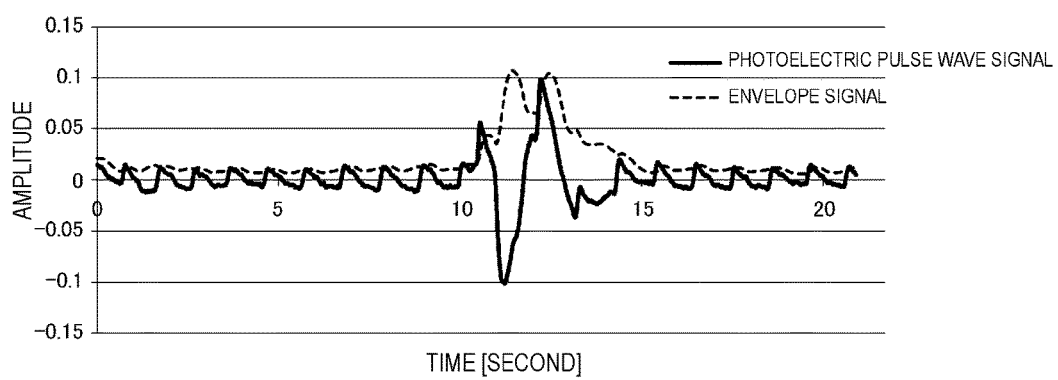
FIG. 3 is a graph illustrating examples of a photoplethysmographic signal and an envelope signal of the photoplethysmographic signal.

An execution result of an envelope detecting method of this manner is illustrated in FIG. 3. FIG. 3 is a graph illustrating examples of the photoplethysmographic signal and the envelope signal of the photoplethysmographic signal. A transverse axis of FIG. 3 indicates time (second) and a longitudinal axis of FIG. 3 indicates amplitude (V). In FIG. 3, the photoplethysmographic signal is indicated by a solid line and the envelope signal is indicated by a dashed line. It should be noted that the envelope of the photoplethysmographic signal, which has been extracted by the envelope detection processor 32, is output to each of the amplitude normalization processor 33 and the filter coefficient update controller 34.

The amplitude normalization processor 33 normalizes amplitude of the photoplethysmographic signal to a desired amplitude value based on amplitude (envelope information) of the envelope. That is to say, the amplitude normalization processor 33 functions as an amplitude normalizing unit in the scope of the disclosure herein. To be more specific, the amplitude normalization processor 33 normalizes the photoplethysmographic waves to the desired amplitude value in accordance with the following equation (1) using the envelope of the photoplethysmographic waves, which has been obtained by the envelope detection processor 32:

Equation 1:

$$ppg_{norm}(t) = d \times ppg(t) / \text{env}_{ppg}(t) \tag{1}$$

wherein d indicates the desired amplitude value, ppg(t) indicates the photoplethysmographic signal to which the HPF 31 has been applied, $\text{env}_{ppg}(t)$ indicates the envelope signal of ppg(t), and $ppg_{norm}(t)$ indicates the normalized photoplethysmographic signal.

Figure 4:
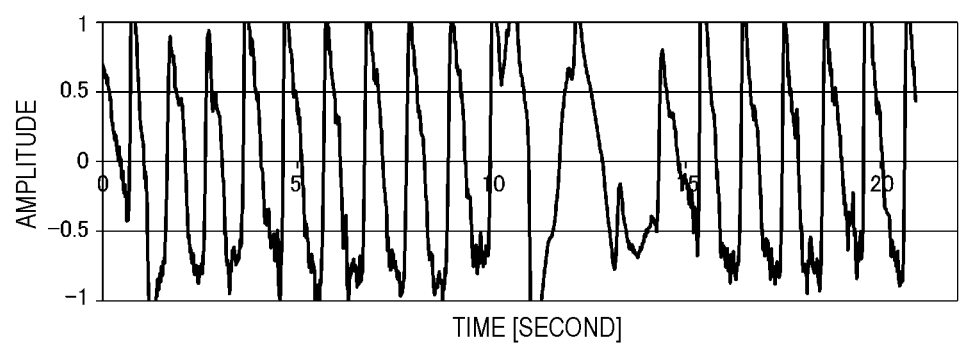
FIG. 4 is a graph illustrating an example of a normalized photoplethysmographic signal.

A waveform normalized in accordance with the equation (1) is illustrated in FIG. 4 (in the case of d=1.0). FIG. 4 is a graph illustrating an example of the normalized photoplethysmographic signal. A transverse axis of FIG. 4 indicates time (second) and a longitudinal axis of FIG. 4 indicates amplitude (V). It should be noted that the photoplethysmographic signal normalized by the amplitude normalization processor 33 is output to the adaptive line spectrum enhancer 35.

The filter coefficient update controller 34 controls execution and stop of the process of updating a filter coefficient of the adaptive line spectrum enhancer 35 based on the amplitude (envelope information) of the envelope of the photoplethysmographic signal. To be more specific, when the amplitude value of the envelope of the photoplethysmographic signal is larger than a first threshold value or the amplitude value of the envelope of the photoplethysmographic signal is smaller than a second threshold value (first threshold value>second threshold value), the filter coefficient update controller 34 stops the update of the filter coefficient of the adaptive line spectrum enhancer 35. On the other hand, when the amplitude value of the envelope of the photoplethysmographic signal is equal to or smaller than the first threshold value and equal to or larger than the second threshold value, the filter coefficient update controller 34 updates the filter coefficient of the adaptive line spectrum enhancer 35. That is to say, the filter coefficient update controller 34 functions as a filter coefficient updating unit in the scope of the disclosure herein. It should be noted that a control signal of the filter coefficient from the filter coefficient update controller 34 is output to the adaptive line spectrum enhancer 35.

The adaptive line spectrum enhancer 35 is one type of the adaptive filter and adapts so as to enhance a linear spectrum on a frequency axis. In other words, the adaptive line spectrum enhancer 35 is configured to vary the filter coefficient, suppress an aperiodic component (for example, artifacts) contained in the normalized photoplethysmographic signal, and allow passage of a periodic component (for example, pulsation component). Further, a cycle of a pulsation interval obtained from the biological signal fluctuates finely even at the rest and a signal of the harmonic component contained in the pulsation signal is therefore suppressed to some extent. The adaptive line spectrum enhancer 35 functions as an adaptive filter in the scope of the disclosure herein. To be more specific, according to the exemplary embodiment, the adaptive line spectrum enhancer 35 includes a delay unit 351, an adaptive filter 352, and an adder 353, as illustrated in FIG. 2.

In the adaptive line spectrum enhancer 35 as illustrated in FIG. 2, the adaptive filter 352 minimizes a mean square error (MSE) of an error signal e[n] as difference between a desired signal d[n] and an output signal y[n], suppresses the aperiodic component (for example, body motion artifacts) contained in the input signal (photoplethysmographic signal), and allows passage of the periodic component (for example, a periodic signal such as photoplethysmographic waves). Further, the delay unit 351 in FIG. 2 is a correlation isolation parameter for removing a correlation present between a noise component of an input signal x[n] and a delayed input signal. The adaptive line spectrum enhancer 35 is connected to the biological information obtainment unit 50 and the output signal from the adaptive line spectrum enhancer 35 is output to the biological information obtainment unit 50. In the embodiment, the adaptive filter 352 employing a fixed point arithmetic operation is used in order to reduce load of an arithmetic operation.

The biological information obtainment unit 50 obtains the biological information such as the pulse rate and the pulse interval, for example, based on the output signal from the adaptive line spectrum enhancer 35 from which the artifacts have been removed. That is to say, the biological information obtainment unit 50 functions as a biological information obtainment unit in the scope of the disclosure herein. It should be noted that the obtained biological information such as the pulse rate is output to the outside or is stored in the above-described RAM.

With the above-described configuration, in the biological information measurement device 1, first, the HPF 31 cuts the DC component of the input photoplethysmographic signal. Then, the envelope detection processor 32 detects the envelope of the photoplethysmographic signal and calculates the amplitude value of the envelope of the photoplethysmographic signal. As described above, in the embodiment, the envelope of the photoplethysmographic signal is calculated by full-wave rectifying the photoplethysmographic signal and applying the LPF 322 to the obtained signal.

Subsequently, the amplitude normalization processor 33 normalizes the photoplethysmographic waves to the desired amplitude value in accordance with the above equation (1) based on the amplitude value of the calculated envelope of the photoplethysmographic signal. Thereafter, the adaptive line spectrum enhancer 35 suppresses the aperiodic component (for example, artifacts) contained in the normalized photoplethysmographic signal and outputs only the periodic component (for example, pulsation component). It should be noted that as described above, the filter coefficient update controller 34 controls updating of the filter coefficient of the adaptive line spectrum enhancer 35.

Then, the biological information obtainment unit 50 obtains the biological information such as the pulse rate and the pulse interval, for example, based on the output signal from the adaptive line spectrum enhancer 35. Thus, the normalization processing by the envelope detection and the adaptive line spectrum enhancer 35 (adaptive filter 352) are combined so as to remove the artifact signal superimposed on the photoplethysmographic signal and extract the pulsation component only.

The embodiment provides an advantage that the LMS method with reduced arithmetic operation load can be employed for the adaptive filter 352 by normalizing the amplitude of the photoplethysmographic waves. The LMS method needs setting of the step-size parameter μ in a range satisfying a convergence condition defined by the following equation (2):

Equation 2

$$0 < \mu < \frac{2}{\sum_{k=0}^{M} E\{x^2[n-k]\}} \quad (2)$$

wherein μ indicates the step-size parameter of the adaptive filter 352, M indicates an order of the adaptive filter 352, x indicates an input biological signal to the adaptive filter 352, and E{ } indicates an arithmetic operation of an expected value.

However, a term (sum of input power) expressed by E in the equation (2) for an aperiodic signal containing the body motion artifacts is previously unknown. In the embodiment, the input photoplethysmographic signal is normalized and has substantially constant amplitude. Therefore, when the order M in the equation (2) is large, the sum of the input power is substantially constant and the step-size parameter μ as the necessary and sufficient condition for convergence of the adaptive filter 352 can be set previously. Further, an adverse effect on the convergence of the adaptive filter 352 by variation in the amplitude of the photoplethysmographic signal (biological signal) due to difference among individuals using the biological information measurement device 1 can be also absorbed.

Therefore, the adaptive filter 352 can be made to adapt appropriately so as to extract only the frequency of the biological signal. Further, even when the artifacts are superimposed continuously, they can be removed by the adaptive filter 352. As a result, the artifacts due to body motion or the like, which have been superimposed on the biological signal, can be removed effectively and the biological information can be obtained robustly against the artifacts.

In addition, the embodiment provides an advantage that a dynamic range of a signal which is input to the adaptive line spectrum enhancer 35 (adaptive filter 352) at the subsequent stage can be determined by normalizing the amplitude of the photoplethysmographic signal. In general, it is difficult for a low-end MCU to execute a floating point arithmetic operation of the adaptive filter 352 because of the arithmetic operation load. For this reason, the fixed point arithmetic operation is required, and in this case, trade-off between arithmetic operation accuracy of the fixed point arithmetic operation for the dynamic range of the input signal and overflow becomes a problem. When a bit number of a decimal part is made large in order to ensure the arithmetic operation accuracy of the fixed point arithmetic operation, overflow occurs in the fixed point arithmetic operation if a large amplitude value is input for the input signal and an accurate arithmetic operation result cannot be obtained. By contrast, when the bit number of the decimal part is made small, arithmetic operation errors are accumulated, resulting in a possibility that the adaptive filter 352 diverges. In the embodiment, normalization of the biological signal to the desired amplitude value at the previous stage of the adaptive filter 352 enables an optimum bit number and an optimum type of the variable of the fixed point arithmetic operation to be determined when the fixed point arithmetic operation is designed. Accordingly, the problem of the dynamic range, which occurs in the fixed point arithmetic operation, can be solved, thereby using the adaptive filter by the low-end MCU.

Moreover, the embodiment provides an advantage that the update of the filter coefficient of the adaptive line spectrum enhancer 35 (adaptive filter 352) can be controlled by using the amplitude value detected by the envelope detection. The normalization processing of the amplitude causes the spectrum of the artifact component to decrease after the normalization. However, when an excessively large or small photoplethysmographic signal is input continuously, a section with an extremely bad SN ratio of the signal lasts, resulting in a possibility that learning of the adaptive filter 352 is adversely influenced. In order to solve this disadvantage, the filter coefficient update controller 34 detects the excessively large or small amplitude value of the photoplethysmographic signal using the output value of the envelope detection processor 32 and operates so as not to update the filter coefficient, thereby preventing inappropriate learning of the adaptive filter 352. In particular, the method using the envelope information for determining the excessively large or small signal utilizes an instantaneous amplitude value of the signal unlike a method using an absolute value of the signal simply for the determination. Therefore, the method can make the determination using a constant amplitude value continuously even at a zero-cross point of the signal and a signal average value.

Second Embodiment

Figure 5:
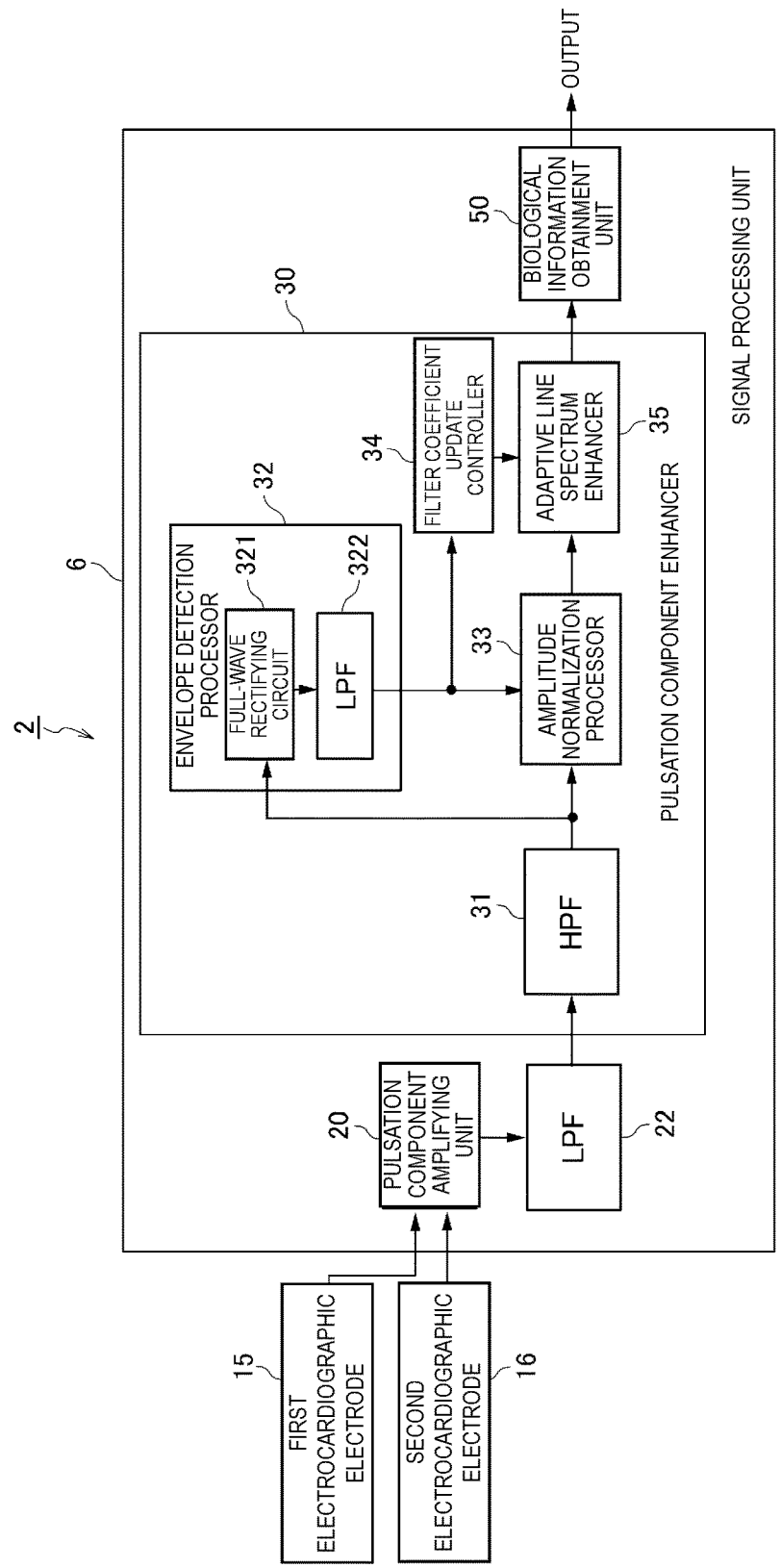
FIG. 5 is a block diagram illustrating the configuration of a biological information measurement device according to a second embodiment.
Figure 6:
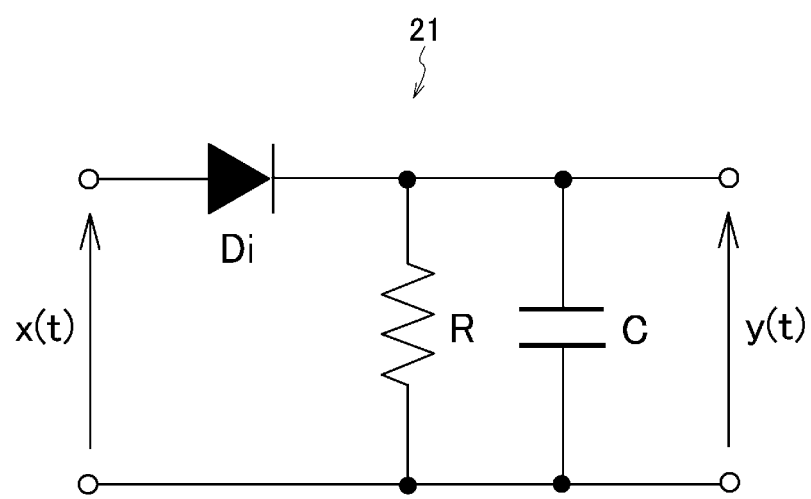
FIG. 6 is a circuit diagram of a diode detecting circuit configuring the biological information measurement device in the second embodiment.

Next, the configuration of a biological information measurement device 2 according to a second embodiment will be described with reference to FIG. 5 and FIG. 6 in combination. Description of the configurations same as or similar to those of the biological information measurement device 1 in the above-described first embodiment are omitted and different points are described mainly. FIG. 5 is a block diagram illustrating the configuration of the biological information measurement device 2 in the second embodiment. In FIG. 5, the same reference numerals denote constituent components that are the same as or equivalent to those in the first embodiment. FIG. 6 is a circuit diagram of a pulsation component amplifying unit 20 (diode detecting circuit 21) configuring the biological information measurement device 2.

The biological information measurement device 2 is different from the above-described biological information measurement device 1 in the following point. That is, in the biological information measurement device 2, the pulsation component amplifying unit 20 and a low-pass filter (LPF) 22 are provided at previous stages of the pulsation component enhancer 30 (HPF 31). They are provided in order to easily adapt to a biological signal with harmonic waves having, as a basic frequency, a pulsation component of an electrocardiographic waveform or a ballistocardiographic waveform for which the adaptive line spectrum enhancer 35 (adaptive filter 352) is difficult to adapt. Further, the biological information measurement device 2 is different from the above-described biological information measurement device 1 also in the following point. That is, the biological information measurement device 2 includes a pair of electrocardiographic electrodes 15 and 16 (first electrocardiographic electrode 15 and second electrocardiographic electrode 16) for detecting an electrocardiographic signal as the biological signal, instead of the photoplethysmographic sensor 10. Other configurations of the biological information measurement device 2 are the same as or similar to those of the above-described biological information measurement device 1, and detail description thereof is omitted.

The first electrocardiographic electrode 15 and the second electrocardiographic electrode 16 detect the electrocardiographic signal, and obtain the electrocardiographic signal in accordance with potential difference between right and left hands of a user when the right and left hands (finger tips) of the user make contact with them. That is to say, the first electrocardiographic electrode 15 and the second electrocardiographic electrode 16 also correspond to the biological signal detecting unit in the scope of the disclosure herein. Each of the first electrocardiographic electrode 15 and the second electrocardiographic electrode 16 is connected to the pulsation component amplifying unit 20 and the detected electrocardiographic signal is amplified by an amplifier (not illustrated), and then, is input to the pulsation component amplifying unit 20.

In the embodiment, the diode detecting circuit 21 as illustrated in FIG. 6 is used for the pulsation component amplifying unit 20. The diode detecting circuit 21 makes peaks remain from an impulse biological signal (electrocardiographic signal) detected by the first electrocardiographic electrode 15 and the second electrocardiographic electrode 16, monotonously decreases the signal between the peaks more moderately than the original biological signal, reduces a harmonic component of a basic frequency contained in the electrocardiographic signal, enhances a signal component of the basic frequency, and outputs the obtained signal to the pulsation component enhancer 30 (to be more specific, outputs the obtained signal to the envelope detection processor 32 and the amplitude normalization processor 33 through the LPF 22 and the HPF 31). The diode detecting circuit 21 (pulsation component amplifying unit 20) functions as a basic frequency amplifying unit as disclosed herein.

Figure 7:
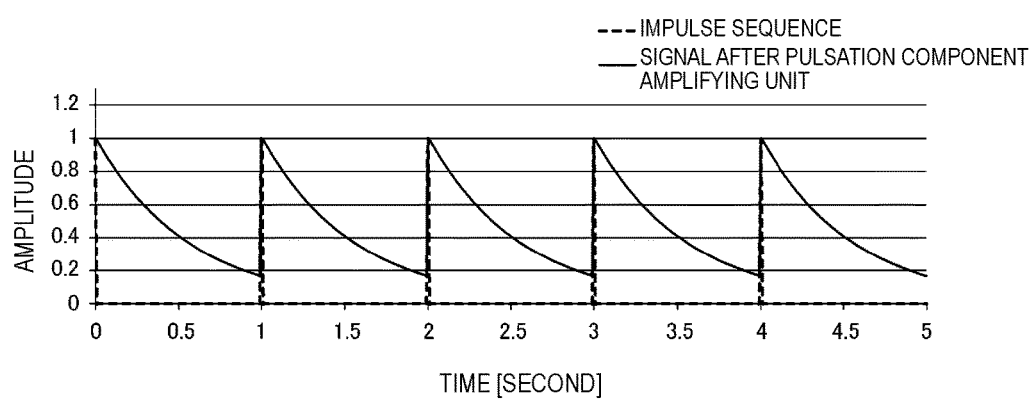
FIG. 7 is a graph illustrating examples of an impulse sequence that is input to the diode detecting circuit and an output signal waveform of the diode detecting circuit.

Examples of an impulse sequence that is input to the diode detecting circuit 21 (pulsation component amplifying unit 20) and an output signal waveform of the diode detecting circuit 21 are illustrated in FIG. 7. In order to simplify the description, the biological signal that is input is assumed to an impulse sequence (60 [bpm], sampling frequency 100 [Hz]) synchronous with pulsation. A transverse axis of FIG. 7 indicates time (second) and a longitudinal axis of FIG. 7 indicates amplitude (V). In FIG. 7, the output signal waveform is indicated by a solid line and the impulse sequence (input signal) is indicated by a dashed line. As illustrated in FIG. 7, the diode detecting circuit 21 is applied to the impulse sequence, so that a waveform with amplified frequency of the pulsation component of the impulse sequence is obtained.

Figure 8:
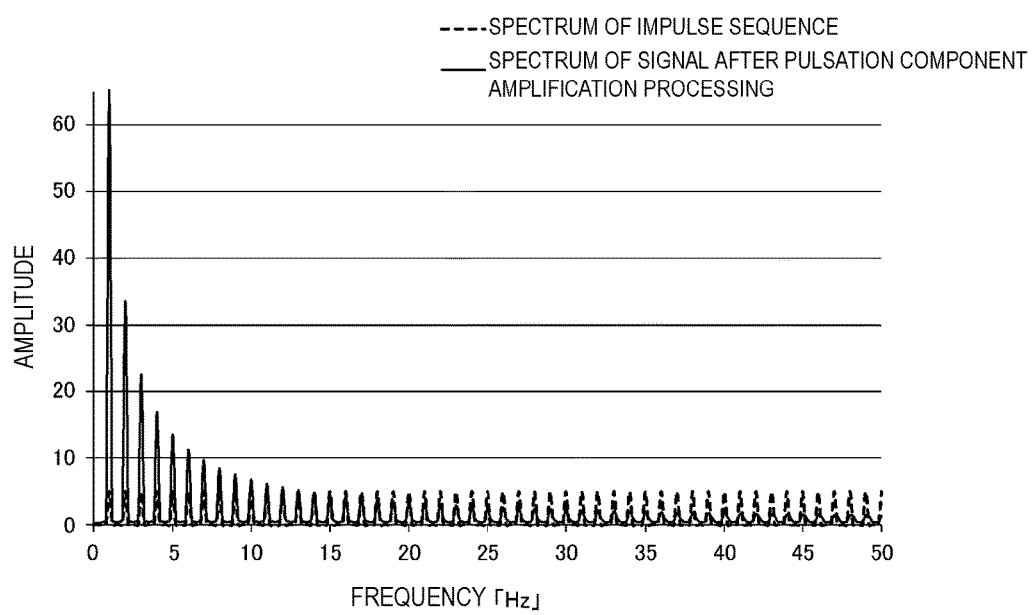
FIG. 8 is a graph illustrating examples of spectra of the impulse sequence that is input to the diode detecting circuit and an output signal from the diode detecting circuit.

FIG. 8 illustrates examples of spectra of the impulse sequences before and after the pulsation component amplification processing, which have been calculated by fast Fourier transform (FFT), that is, the spectrum of the impulse sequence that is input to the diode detecting circuit 21 (pulsation component amplifying unit 20) and the spectrum of an output signal from the diode detecting circuit 21. A transverse axis of FIG. 8 indicates frequency (Hz) and a longitudinal axis of FIG. 8 indicates amplitude. In FIG. 8, the spectrum of the output signal is indicated by a solid line and the spectrum of the impulse sequence (input signal) is indicated by a dashed line. With reference to FIG. 8, it is found that the spectrum of the pulsation component at 1 [Hz] is amplified after the diode detection processing (note that a DC component is cut from the signal after the pulsation component amplification processing, and then, the spectrum thereof is calculated).

The diode detecting circuit 21 is not used for detecting the envelope normally but for amplifying the spectrum of the pulsation component by discharging electric charges accumulated in a capacitor C to some extent without holding the impulse sequence between the peaks intentionally. Therefore, a constant of the diode detecting circuit 21 as illustrated in FIG. 6 needs to be set to such constant that the electric charges accumulated in the capacitor C are discharged to some extent even when the electrocardiographic signal corresponding to a measureable maximum pulse rate in specification is input. It should be noted that signal processing in the diode detecting circuit 21 may be executed not by an electric circuit but by digital signal processing.

Figure 9:
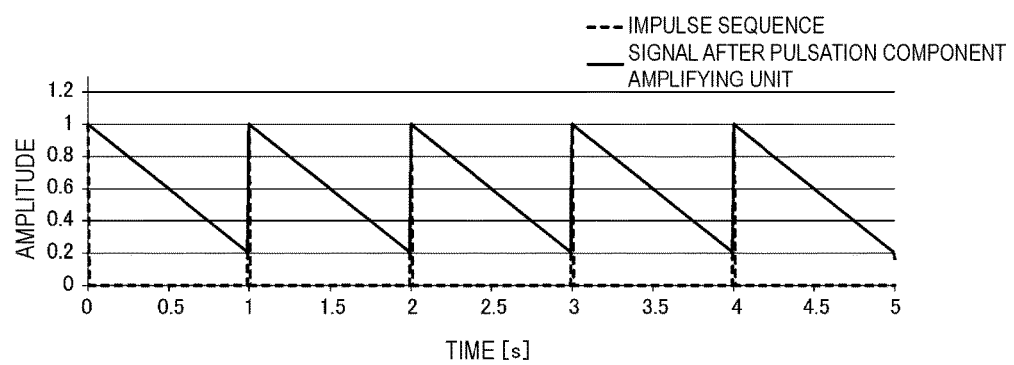
FIG. 9 is a graph for explaining another example of a pulsation component amplifying method.

Further, the pulsation component amplifying unit 20 may not be configured by the diode detecting circuit 21 and may perform the following processing. That is, the pulsation component amplifying unit 20 may perform processing of functioning like the diode detecting circuit 21 in the case in which a voltage of the input signal is increased and generating sawtooth waves so as to monotonously decrease the signal by a constant inclination in the case in which the voltage of the input signal is decreased. FIG. 9 is a graph for explaining another example of the pulsation component amplifying method. A transverse axis of FIG. 9 indicates time (second) and a longitudinal axis of FIG. 9 indicates amplitude (V). In FIG. 9, an output signal waveform is indicated by a solid line and an impulse sequence (input signal) is indicated by a dashed line.

Application of the diode detecting circuit 21 (pulsation component amplifying unit 20) provides an effect that the spectrum of the pulsation component is amplified and an effect that an artifact signal smaller than the signal after the pulsation component amplification as illustrated in FIGS. 7 and 9 can be removed as a result. With this, a signal robust against the artifacts can be obtained. Further, an artifact signal larger than the signal after the pulsation component amplification as illustrated in FIGS. 7 and 9 is also reduced by the adaptive line spectrum enhancer 35 (adaptive filter 352) at the subsequent stage. It should be noted that the output signal from the diode detecting circuit 21 is output to the LPF 22.

Figure 10:
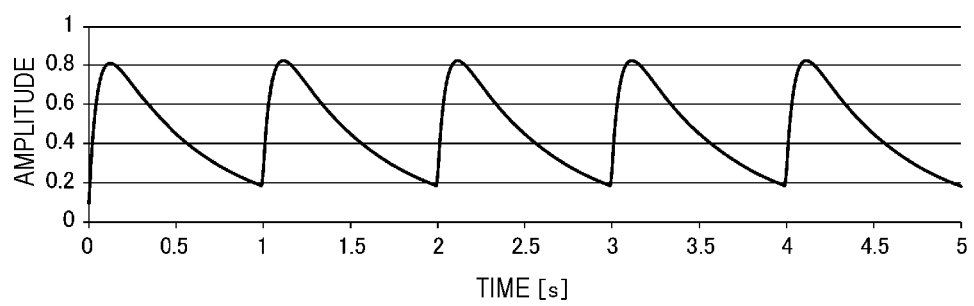
FIG. 10 is a graph illustrating an example of an output signal from an LPF.

The LPF 22 is provided at a subsequent stage of the diode detecting circuit 21, allows selective passage of the signal component of the basic frequency contained in the electrocardiographic signal output from the diode detecting circuit 21, and suppresses passage of the harmonic component (high-frequency component) of the basic frequency. When a measureable maximum pulse rate in specification is set to 200 [bpm], a cutoff frequency of the LPF 22 is preferably set to be equal to or higher than 3.333 [Hz]. A signal waveform when the LPF 22 is applied to the signal after experienced the diode detecting circuit 21 is illustrated in FIG. 10. FIG. 10 is a graph illustrating an example of the output signal from the LPF 22. A transverse axis of FIG. 10 indicates time (second) and a longitudinal axis of FIG. 10 indicates amplitude (V). The output signal from the LPF 22 is output to the pulsation component enhancer 30. The configurations of the pulsation component enhancer 30 and the biological information obtainment unit 50 are the same as or similar to those of the above-described biological information measurement device 1, and detail description thereof is therefore omitted.

Thus, even the biological signal with the harmonic waves having, as the basic frequency, the pulsation component of the electrocardiographic waveform or the ballistocardiographic waveform for which the adaptive line spectrum enhancer 35 (adaptive filter 352) is difficult to adapt normally can be converted into a signal (signal having the pulsation component as a main component) for which the adaptive line spectrum enhancer 35 (adaptive filter 352) is easy to adapt by applying the pulsation component amplifying unit 20 (diode detecting circuit 21) and the LPF 22 to the signal.

As described above, with the embodiment, the basic frequency component of the electrocardiographic signal is amplified by the pulsation component amplifying unit 20 (diode detecting circuit 21). Therefore, even when the biological signal (for example, the biological signal with the harmonic waves of the electrocardiographic waveform or the ballistocardiographic waveform) having characteristics that the adaptive filter 352 is difficult to adapt for it is input, the adaptive filter 352 can be made to adapt for the biological signal. Accordingly, the biological information can be obtained stably from the biological signal superimposed with the artifacts.

In addition, in the embodiment, the spectrum of the basic frequency of the electrocardiographic signal can be further enhanced by applying the LPF 22 to the electrocardiographic signal output from the diode detecting circuit 21. Note that the LPF 22 allows selective passage of the signal component of the basic frequency contained in the electrocardiographic signal and suppresses passage of the harmonic component of the basic frequency.

Although the embodiments of the invention have been described above, the invention is not limited to the above-described embodiments and various modifications can be made. For example, in the above-described embodiments, the method using the full-wave rectifying circuit 321 and the LPF 322 is employed as the envelope detection method. Alternatively, instead of the method, for example, various methods such as a method using a diode detecting circuit, a method using a synchronous detecting circuit, a method in which an input signal is squared, and then, the LPF is applied to the signal, and a method in which instantaneous amplitude is calculated from an analysis signal by a Hilbert transformation device or quadrature demodulation can be used.

Although in the above-mentioned embodiments, a method in which the update of the filter coefficient is stopped based on the threshold values is employed in the update control of the filter coefficient of the adaptive filter 352 based on the envelope information (the amplitude value of the envelope), for example, a method in which the step-size parameter in accordance with the amplitude value is dynamically set may be used instead of the method. In this case, the reference to the step-size parameter in accordance with the amplitude value can be performed by a method involving calculating the step-size parameter from the amplitude value or a method involving referring to a lookup table that is previously stored.

REFERENCE SIGNS LIST 1, 2 BIOLOGICAL INFORMATION MEASUREMENT DEVICE
5, 6 SIGNAL PROCESSING UNIT
10 PHOTOPLETHYSMOGRAPHIC SENSOR
15 FIRST ELECTROCARDIOGRAPHIC ELECTRODE

16 SECOND ELECTROCARDIOGRAPHIC ELECTRODE
20 PULSATION COMPONENT AMPLIFYING UNIT
21 DIODE DETECTING CIRCUIT
22 LPF
30 PULSATION COMPONENT ENHANCER
31 HPF
32 ENVELOPE DETECTION PROCESSOR
321 FULL-WAVE RECTIFYING CIRCUIT
322 LPF
33 AMPLITUDE NORMALIZATION PROCESSOR
34 FILTER COEFFICIENT UPDATE CONTROLLER
35 ADAPTIVE LINE SPECTRUM ENHANCER
351 DELAY UNIT
352 ADAPTIVE FILTER
50 BIOLOGICAL INFORMATION ACQUIRING UNIT

The invention claimed is:

1. A biological information measurement device comprising:
    at least one sensor configured to detect a photoplethysmographic signal as a biological signal using light absorption characteristics of hemoglobin in blood;
    an envelope detecting circuit that receives the biological signal and generates an envelope of the biological signal; and
    a computer processing unit configured to:
        normalize an amplitude of the biological signal based on an amplitude of the envelope,
        filter an aperiodic component contained in the normalized biological signal and output a periodic component of the normalized biological signal, and
        obtain biological information based on the periodic component of the normalized biological signal.

2. The biological information measurement device according to claim 1, wherein the computer processing unit comprises an adaptive filter having a variable filter coefficient for filtering the aperiodic component contained in the normalized biological signal.

3. The biological information measurement device according to claim 2, wherein the computer processing unit further comprises:
    a delay device coupled to an input of the adaptive filter and configured to delay the normalized biological signal; and
    an adder coupled to an output of the adaptive filter,
    wherein the adaptive filter minimizes a mean square error of an error signal output by the adder as difference between a desired signal and an output signal of the adaptive filter.

4. The biological information measurement device according to claim 2, wherein the computer processing unit is further configured to update the variable filter coefficient of the adaptive filter based on the amplitude of the envelope.

5. The biological information measurement device according to claim 4, wherein the computer processing unit stops the update of the variable filter coefficient when the amplitude of the envelope is larger than a first threshold value or smaller than a second threshold value.

6. The biological information measurement device according to claim 1, wherein the envelope detecting circuit includes:
    a full-wave rectifying circuit that rectifies the biological signal, and
    a low-pass filter passes a low-frequency component contained in the rectified biological signal and generates the envelope of the rectified biological signal.

7. The biological information measurement device according to claim 1, further including a frequency amplifying unit that maintains peaks from an impulse biological signal detected by the biological signal detecting unit, monotonously decreases the signal between the peaks, reduces a harmonic component of a basic frequency contained in the biological signal, amplifies a signal component of the basic frequency, and outputs the signal to the envelope detecting circuit and the computer processing unit.

8. The biological information measurement device according to claim 7, further including a low-pass filter interposed at a subsequent stage of the frequency amplifying unit, wherein the low-pass filter passes the signal component of the basic frequency contained in the biological signal output from the frequency amplifying unit, and filters the harmonic component of the basic frequency.

9. The biological information measurement device according to claim 8, wherein the biological signal detecting unit comprises a pair of electrocardiographic electrodes configured to detect the biological signal and coupled to an input of the frequency amplifying unit.

10. The biological information measurement device according to claim 9, wherein the frequency amplifying unit comprises a diode detecting circuit have at least one diode coupled to one of the pair of electrocardiographic electrodes and a resistor and capacitor each coupled in parallel to respective outputs of the pair of electrocardiographic electrodes.

11. The biological information measurement device according to claim 1, wherein the at least one sensor comprises a light emitting unit that emits light based on a pulsed driving signal, a light receiving unit that outputs a detection signal based on an intensity of light emitted from the light-emitting element, and an amplifying unit that amplifies the detection signal as the biological signal.

12. The biological information measurement device according to claim 11, further comprising a high-pass filter that filters a direct-current component of the amplified signal and outputs the filtered signal as the biological signal to the envelope detecting circuit and the computer processing unit.

13. A method for measuring biological information, the method comprising:
    detecting, by a biological signal detecting unit, a biological signal;
    generating, by an envelope detecting circuit, an envelope of the biological signal;
    normalizing, by a computer processing unit, an amplitude of the biological signal based on an amplitude of the envelope;
    filtering, by an adaptive filter having a variable filter coefficient, an aperiodic component contained in the normalized biological signal and outputting a periodic component of the normalized biological signal; and
    obtaining, by the computer processing unit, biological information based on the periodic component of the normalized biological signal.

14. The method for detecting biological information according to claim 13, further comprising, updating, by the computer processing unit, the variable filter coefficient of the adaptive filter based on the amplitude of the envelope.

15. The method for detecting biological information according to claim 14, further comprising, stopping, by the computer processing unit, the update of the variable filter coefficient when the amplitude of the envelope is larger than a first threshold value or smaller than a second threshold value.

16. The method for detecting biological information according to claim 13, further comprising:
- a full-wave rectifying, by the envelope detecting circuit, the biological signal; and
- passing, by the envelope detecting circuit, a low-frequency component contained in the rectified biological signal to generate the envelope of the rectified biological signal.

17. The method for detecting biological information according to claim 13, further comprising:
- maintaining, by a frequency amplifying unit, peaks from an impulse biological signal detected by the biological signal detecting unit;
- monotonously decreasing, by the frequency amplifying unit, the signal between the peaks;
- reducing, by the frequency amplifying unit, a harmonic component of a basic frequency contained in the biological signal;
- amplifying, by the frequency amplifying unit, a signal component of the basic frequency; and
- outputting, by the frequency amplifying unit, the signal to the envelope detecting circuit and the computer processing unit.

18. The method for detecting biological information according to claim 17, further comprising:
- passing, by a low-pass filter interposed at a subsequent stage of the frequency amplifying unit, the signal component of the basic frequency contained in the biological signal output from the frequency amplifying unit; and
- filtering, by the low-pass filter, the harmonic component of the basic frequency.

19. The method for detecting biological information according to claim 18, wherein the biological signal detecting unit comprises a pair of electrocardiographic electrodes for detecting the biological signal.

20. The method for detecting biological information according to claim 13, further comprising:
- filtering, by a high-pass filter, a direct-current component of the biological signal detecting by the biological signal detecting unit; and
- outputting the filtered signal as the biological signal to the envelope detecting circuit and the computer processing unit.

* * * * *